United States Patent
Legendre et al.

(10) Patent No.: US 9,476,857 B2
(45) Date of Patent: *Oct. 25, 2016

(54) METHOD AND APPARATUS FOR REMOVAL OF THE DOUBLE INDICATION OF DEFECTS IN REMOTE EDDY CURRENT INSPECTION OF PIPES

(71) Applicant: Schlumberger Technology Corporation, Sugar land, TX (US)

(72) Inventors: Emmanuel Legendre, Sevres (FR); Thilo M Brill, Feucherolles (FR); Richard A. Rosthal, Richmond, CA (US); Gerald N. Minerbo, Missouri City, TX (US)

( * ) Notice: Subject to any disclaimer, the term of this patent is extended or adjusted under 35 U.S.C. 154(b) by 16 days.

This patent is subject to a terminal disclaimer.

(21) Appl. No.: 14/590,921

(22) Filed: Jan. 6, 2015

(65) Prior Publication Data
US 2015/0127274 A1 May 7, 2015

Related U.S. Application Data

(63) Continuation of application No. 13/266,129, filed as application No. PCT/EP2010/003800 on Jun. 25, 2010, now Pat. No. 8,958,989.

(30) Foreign Application Priority Data

Jun. 30, 2009 (EP) ..................... 09290508

(51) Int. Cl.
*G01V 1/40* (2006.01)
*G01N 27/90* (2006.01)
*E21B 47/08* (2012.01)
*G01B 7/06* (2006.01)
*E21B 49/00* (2006.01)

(52) U.S. Cl.
CPC ........... *G01N 27/902* (2013.01); *E21B 47/082* (2013.01); *E21B 49/003* (2013.01); *G01B 7/10* (2013.01); *G01N 27/9046* (2013.01); *G01N 27/9073* (2013.01); *G01N 27/9086* (2013.01)

(58) Field of Classification Search
CPC .... E21B 47/082; G01B 7/10; G01N 27/9046
See application file for complete search history.

(56) References Cited

U.S. PATENT DOCUMENTS

| | | | | |
|---|---|---|---|---|
| 4,292,588 A | * | 9/1981 | Smith | G01B 7/10 324/221 |
| 5,987,385 A | * | 11/1999 | Varsamis | E21B 47/0002 702/6 |
| 8,958,989 B2 | * | 2/2015 | Legendre | E21B 47/082 702/6 |
| 2012/0095686 A1 | | 4/2012 | Legendre | |

* cited by examiner

*Primary Examiner* — Elias Desta
(74) *Attorney, Agent, or Firm* — Michael Dae

(57) ABSTRACT

The apparatus employs the remote field eddy-current (RFEC) inspection technique to electromagnetically measure physical parameters of a metallic pipe. RFEC devices inserted into and displaced along a cylindrical pipes may be used to measure the ratio of pipe thickness to electromagnetic skin-depth and thus allow for the non-invasive detection of flaws or metal loss. Typically these RFEC thickness measurements exhibit a so-called double-indication of flaws, an undesired artifact due to a double-peaked geometrical sensitivity function of the device.

The method describes a means by which this double indication artifact may be removed by an appropriate processing of RFEC measurements performed by an apparatus specifically designed for this purpose. The invention is particularly well designed for applications in the oilfield industry.

18 Claims, 6 Drawing Sheets

METHOD AND APPARATUS FOR REMOVAL OF THE DOUBLE INDICATION OF DEFECTS IN REMOTE EDDY CURRENT INSPECTION OF PIPES

This is a continuation application of co-pending U.S. patent application Ser. No. 13/266,129 to Emmanuel Legendre, filed under national phase of PCT/EP2010/003800 on Jun. 25, 2010 which claims priority of EP09290508.2 filed on Jun. 30, 2009, and entitled "Method and Apparatus for Removal of The Double Indication of Defects in Remote Eddy Current Inspection of Pipes," which is hereby incorporated in its entirety for all intents and purposes by this reference.

BACKGROUND

This application relates to a method and apparatus for detecting corrosion loss in well bore tubulars; more specifically, this method and apparatus relate to the removal of double indication of defects from varying tubular geometries while performing remote field eddy current non-destructive inspection of such tubulars.

INTRODUCTION AND PRIOR ART

The inspection tool can be a mechanical caliper, an ultrasonic tool or an electromagnetic tool. The mechanical caliper comprises a plurality of fingers for sensing the inner geometry of the casing. The mechanical calipers cannot be used for the determination of casing thickness, cannot distinguish non-metallic deposits on the casing from the metallic casing itself, and may initiate corrosion by scratching the casing surface. The ultrasonic tool measures the time-of-flight of a sound-pulse between emission by the tool, reflections at the inner and outer surfaces of the casing and reception by the sound-wave detectors in the tool. They may measure the inside diameter as well as the thickness of the casing. The ultrasonic tool cannot be used when the casing transports a fluid mixture comprising a certain quantity of gas relatively to liquid, and provides deteriorated reflected signals in the presence of surface roughness that typically arise in corroded casing.

The electromagnetic tool is a non-destructive inspection tool. It may be based either on the flux-leakage principle, the eddy-current principle or a combination thereof. The electromagnetic tool is insensitive to non-conductive deposits and can operate irrespective of the nature of the fluid mixture flowing into the casing.

The electromagnetic tool based on flux-leakage principle is typically used for the detection of localized damage in ferromagnetic pipes. This tool commonly subjects the casing to a strong static magnetic field. Due to the ferromagnetic nature of the casing, the magnetic return flux is mainly confined to the inside of the metal casing. In the presence of discontinuities in the metal, such as pits and holes caused by corrosion, the magnetic flux "leaks" out of the body of the metal and may be detected with appropriate magnetic sensors such as coils, Hall probes, or magneto-resistive sensors. See, U.S. Pat. No. 6,924,640 to Fickert et al. issued Aug. 2, 2005 for deployment of Hall-effect sensors. To allow for sufficiently sensitive and quantitative measurements, the flux-leakage based tool requires strong magnetic fields and good flux coupling into the inspected body. This implies close proximity of the magnetic field source to the inner casing surface. For further description of this method, one might review U.S. Pat. No. 3,940,689 to Johnson, issued Feb. 24, 1976 describing a flux-leakage and eddy current sensing device, which patent is incorporated by reference herein to further describe the background of this invention. The combinations of casings and tubing used in hydrocarbon wells often exhibit varying pipe diameters that render the requirements of sufficiently strong and well-coupled magnetic flux difficult to maintain. Furthermore, magnetic flux-leakage tools are not suitable for measurements of gradual thinning of pipes.

The electromagnetic tool based on eddy-current principle is well suited for the measurement of both, inside diameter and wall thickness of ferromagnetic metallic casing. See, for example, the description of the thickness coils in U.S. Pat. No. 4,292,588 to Smith, issued Sep. 29, 1981, describing eddy current measurement of well bore tubulars. This tool excites an alternating current in a coil transmitter adapted for inducing eddy-currents in the surrounding conductive casing and measures the induced voltage in a separate receiver coil. Alternatively, the tool may measure the impedance of the transmitter coil. The transimpedance is affected by the casing magnetic permeability ($\mu$), electrical conductivity ($\sigma$) and the inner diameter of the nearby casing. In the case of electromagnetic tool where sufficiently low frequencies and large coil separations are used, measurement of the transimpedance is used to extract the ratio of wall thickness d of the casing to skin depth $\delta$, the so-called electromagnetic thickness (EM thickness) d/$\delta$.

SUMMARY OF INVENTION

This apparatus for measuring ferromagnetic tubular thickness uses remote field eddy current sensing and is made up of a body connected on a wireline for insertion in a well bore tubular having a transmitter coil and a plurality of symmetrically situated receiver device on opposing sides of the transmitter coil; a circuit for energizing the transmitter coil at a selectable frequency; a circuit for receiving a signal from each receiver device and for processing the signal to eliminate a double indication of flaws.

Each receiver device is preferably a coil centered on the longitudinal axis of the apparatus. The apparatus provides the ability to the user allowing the frequency to be selectable between 8.75, 17.5, 35, and 70 Hz, which has been identified as low enough to permit the electromagnetic force to penetrate the downhole tubular or casing and is designed to operate when the electromagnetic thickness, i.e. the ratio of the tubular wall thickness to the skin depth of the material, is equal to or less than five (5). The receiver coils are spaced a distance which, when divided by the inner diameter of the tubular, is greater than or equal to 2.5. For most tubulars or casing used in the oil fields, this suggests a frequency range between 8.75 and 70 Hz and a transmitter/receiver spacing of no less than 25 inches.

The apparatus preferably provides a four symmetrically spaced receiver coils, each pair spaced on opposing sides of the transmitter coil a distance of L1=k1×dz and L2=k2×dz, where k1 and k2 have no common divisor and dz is an incremental length along the longitudinal axis of the apparatus. The circuit for receiving a signal and for processing the signal to eliminate a double indication of flaws can be a programmable digital computer providing a central processor, providing a memory and connections to a analog to digital convertor for digitizing the signal to discrete data for processing by the programmable digital computer.

The apparatus can also consist of receivers selected from the one of the following: coils, Hall effect voltage detectors, and magnetoresistive sensors without departing from the spirit or intent of this disclosure.

Generally, this apparatus for measuring defects in a well bore pipe using remote field eddy current measurement provides a transmitter coil and a plurality of receiver coils in spaced axial relationship from each other; a circuit generating a transmitter current and sensing a receiver voltage at each of the plurality of receiver coils collecting a convoluted signal proportional to the thickness of the pipe adjacent each receiver coil; and, a data analysis circuit which deconvolutes each sensed signal to remove ghost-image signals from such receiver signal. Preferably, the receiver coils are symmetrically located on opposing sides of the transmitting coil. A preferred arrangement for this apparatus for measuring defects in a pipe using remote field eddy current measurement comprises a transmitter providing a selectable low frequency electromotive force; a pair of receiver coils spaced longitudinally on a first side of the transmitter and a pair of receiver coils spaced longitudinally on a second side of the transmitter each pair of coils symmetrically matched with the similarly situated receiver coil on the opposing side of the transmitter; a circuit for correlating the transmitter current and the receiver voltages, as the apparatus is moved through the pipe; thereby permitting the circuit to measure phase deviations of a transimpedance as the apparatus moves past the same point in the pipe allowing the duplicate image to be eliminated and the impulses transmitted and received by the transmitter to be averaged lowering a signal to noise ratio for the measurement of receiver voltage.

The apparatus allows a method for removing ghost defects from a remote field eddy current sensing device comprising generating from a transmitter an eddy current on a well bore tubular outer surface; detecting the eddy current signal with more than one remote receiver; generating an eddy current signal on a well bore tubular outer surface from an incrementally different position; detecting the eddy current with the more than one remote receiver from the incrementally different position; determining a linear combination of eddy current signals detected by the more than one remote receiver to eliminate ghost defects in such received signals.

Essentially, this method for removing ghost defects from a remote field eddy current sensing device providing a transmitting coil and a plurality of symmetrically placed receiving coils on a longitudinal axis of the device provides the steps of exciting the transmitting coil in a well bore tubular with a low frequency current to induce an eddy current in the well bore tubular; sensing an induced electromotive force at the plurality of receiving coils in a spaced relation with the transmitting coil at a first location; storing a sensed signal from each receiving coil at the first location; repeatedly moving the transmitting coil in the well bore tubular to a new discrete location and sensing the induced electromotive force at the plurality of receiving coils for each movement of the transmitting coil; saving each sensed signal from each receiving coil at the plurality of locations; and, manipulating the saved signal from each sensed coil to eliminate the duplicate readings. This processing can be accomplished in real time or stored in the memory and processed at a later time or compared with earlier runs in the same well bore tubular to detect long-term degradation in the thickness of the tubular. The method preferably provides four equal coils placed on opposing sides of a transmitting coil and spaced a distance L from the transmitting coil which is at least 2.5 times the inner diameter of the tubular to be measured and the electromagnetic thickness of the tubular to be measured is less than or equal to 5.

DETAILED DESCRIPTION OF AN EMBODIMENT OF THE INVENTION

Figure 1:
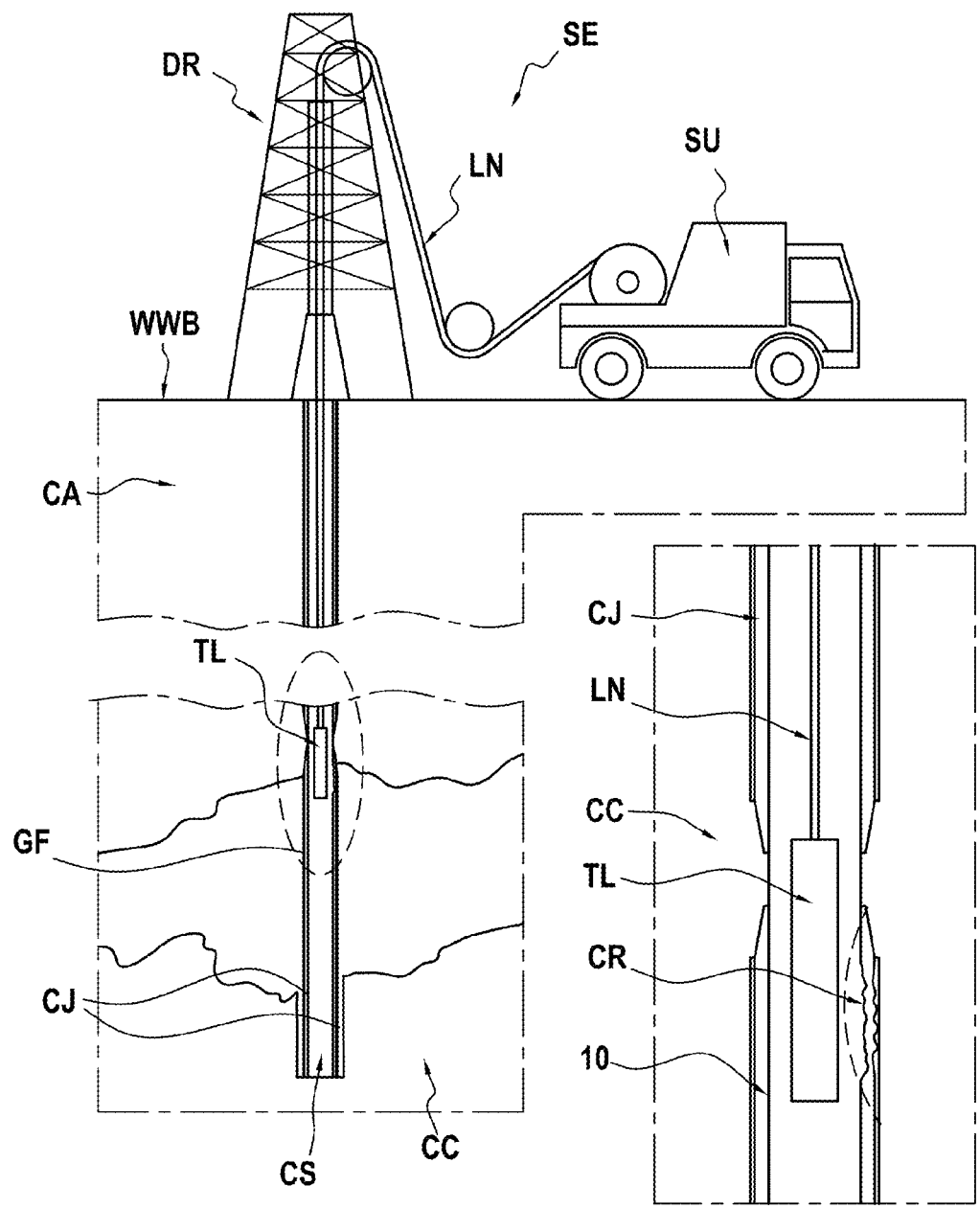
FIG. 1 schematically shows a typical onshore hydrocarbon well location and an enlarged portion of a zone where measurements are performed by a standard wireline device or tool.
Figure 2:
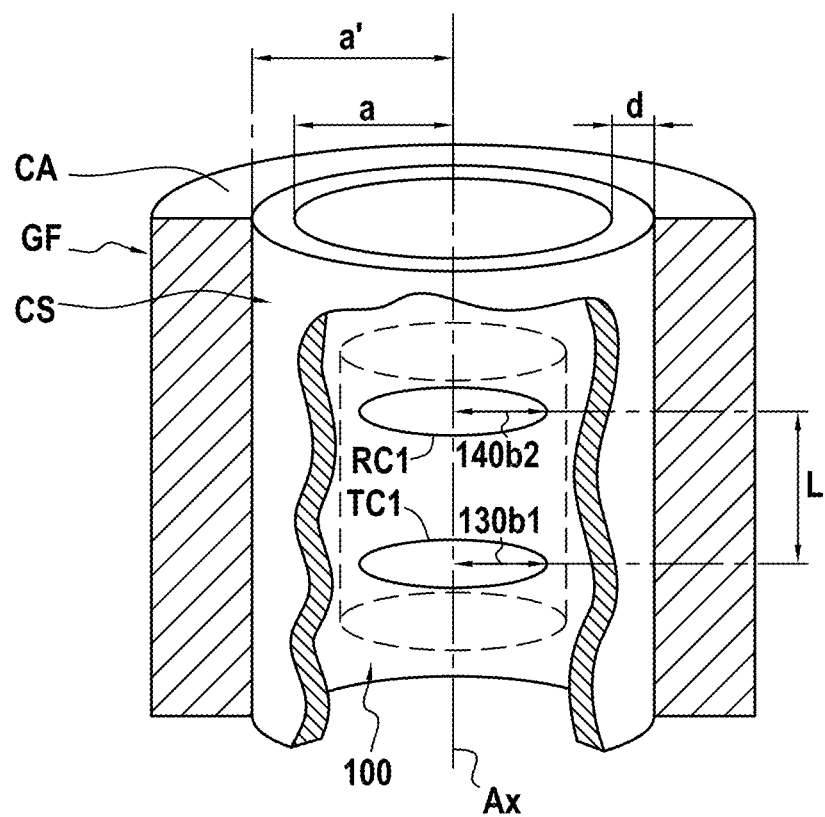
FIG. 2 is a cross section view of a casing schematically showing the measuring arrangement of the invention.

FIG. 2 shows schematically the measuring arrangement 1 according to a preferred embodiment of the invention. The measuring arrangement 1 is fitted within the logging tool TL illustrated in FIG. 1.

In the preferred embodiment of the invention all measurements of the tool are based on the determination of the transimpedance Z which is defined as the mutual impedance between the transmitter current I and the receiver voltage V of a given transmitter-receiver pair:

$$Z = \frac{V}{I} \qquad \text{Eq. (1)}$$

The tool response may be compared to that of a poorly coupled and lossy transformer where the transmitter of the primary circuit induces a voltage in the receiver coil of the secondary circuit. This mutual inductance coupling is composed of flux-coupling through the medium inside the casing and of contributions by flux passing through the metal and outside of the pipe. The electromagnetic field is strongly affected by eddy-currents inside the metal, which flow circumferentially virtually uninhibited. The magnetic field inside the casing has a dominating axial component. Changes in the properties of the metal—such as the thickness—manifest themselves in corresponding changes of the transimpedance Z.

Preferably, an air-calibration is performed. The calibrated measurement ratio M can be defined as:

$$M = \frac{Z}{Z_{air}} = \frac{V/I}{V_{air}/I_{air}} \qquad \text{Eq. (2)}$$

The calibrated measurement ratio M is advantageous because the ratio M becomes insensitive to biases due to the measuring arrangement realization. The biases are typically caused by the number of turns in the coils and effect of metallic parts, such as metallic sleeves and the measuring arrangement body. However, the calibrated measurement ratio M does not compensate for variations of the air or casing measurement due to temperature, pressure, and drift in the electronic arrangement.

In general, we can decompose the transimpedance Z or the ratio M either into a in-phase (real) component R and out-of-phase (imaginary) component R or into a real amplitude A and relative phase $\phi$, for instance $$Z = \frac{V}{I} = R + iX = A\exp(i\varphi). \qquad \text{Eq. (3)}$$

The measuring arrangement 100 is shown schematically in FIG. 2. The tool provides a transmitter coil 110 and receiver coils 120 (only one of which is shown in this drawing) situated on the longitudinal axis of the tool Ax. In the preferred embodiment of the invention all transmitters and receivers are solenoids with axes parallel or equal to the tool axis Ax. As previously noted, receivers may alternatively be solid state devices such as Hall-effect, magnetoresistive devices or other magnetic field sensors.

A transimpedance is determined for each pair defined by a given receiver coil and the single transmitter. As is well known by those having ordinary skill in this art, all coils are characterized by a coil geometry, such as number of turns of the coils, length of coils, winding radii and wire gauges. Additionally, the relative position of a given transmitter-receiver pair is determined by the mutual spacing L along the tool axis Ax.

Furthermore, a measurement is characterized by the operating frequency, which may be a multitude of user-selectable frequencies. The measurement arrangement is designed specifically to optimize the sensitivity of the transimpedance measurement to the desired physical parameter, which is the average EM thickness of a given cross-section of the pipe.

It is convenient to use dimensionless variables to classify the response of the pipe to the various sensor geometries and frequencies. We already mentioned the pipe EM thickness is the ratio d/δ where d is the pipe thickness d='-a (see FIG. 2), the skin depth δ is given by $$\delta = \sqrt{\frac{2}{\sigma\mu\omega}}, \qquad \text{Eq. (4)}$$

with the casing magnetic permeability μ and electrical conductivity σ for a transmitter angular frequency of ω=2πf. A second dimensionless quantity L/(2a) describes the sensor spacing relative to the pipe diameter.

Remote Field Eddy Current Regime

For small ratio $$\frac{d}{\delta} \leq 5 \qquad \text{Eq. (5)}$$

—the large skin-depth limit—the electromagnetic fields can penetrate the pipe wall thickness and radiate into the region outside the casing (medium 3)—considered to be homogenous. This requires sufficiently low excitation frequencies (see below).

If additionally the spacing L between transmitter coil TC1 and receiver coil RC1 is sufficiently large, approximately given by $$L/(2a) \geq 2.5, \qquad \text{Eq. (6)}$$

the phase $\phi$ of the transimpedance measurement becomes nearly a linear function of the pipe EM thickness, given approximately by $$\varphi = 2\frac{d}{\delta} = 2d\sqrt{\frac{\sigma\mu\omega}{2}}. \qquad \text{Eq. (7)}$$

This is the so-called remote-field eddy-current (RFEC) regime. In this regime, the direct waveguide-beyond-cutoff-like coupling between transmitter and receiver inside the pipe is sufficiently attenuated that the transimpedance response becomes dominated by the field which has penetrated the pipe into the external medium 3 near the transmitter (picking up one phase shift of d/δ), propagated nearly dipole-radiation-like within medium 3 and finally re-entered across the pipe into medium 1 near the receiver (picking up a second phase shift of d/δ). Measurements by the tool of phase $\phi$ are thus used to invert for the EM thickness of the pipe. The upper limit of L/(2a) is a function of the signal-to-noise ratio (SNR) of the measurement. The voltage signal at the receiver is proportional to a complex propagation factor exp(ik 2 d), where k=(1−i)/δ and where 2d is the double path through the casing. More generally written as $$Z = \frac{\exp(-2kd)}{L^3} f(d/\delta, ID, \mu/\sigma, L, b_1, b_2) \qquad \text{Eq. (8)}$$

where the dominating exponential has been separated, the remaining parameters in function $f(\ )$ depend on the geometry of the tool and the casing properties. The parameters $b_1$ 130 and $b_2$ 140 are the mean transmitter and receiver radii, ID (=2a in FIG. 2) is the inner diameter of the casing, μ/σ is the ratio of magnetic permeability to conductivity of the casing—the so-called electromagnetic properties of the casing. Inspection of Eq. (8) indicates that both amplitude and phase are characterized by the same quantity 2d/δ.

Even if multiple casings are present, the measurements obtained by this apparatus still provide the total EM thickness, including the contributions from outer metal pipes, as long as the field penetrating all layers can be detected with a sufficient SNR. Comparisons between logs run at different times ("time-lapse") can thus provide information on gradual metal loss of the combined pipes. This method has long been used in single strings corrosion detection systems.

Design Summary

The typical dimensionless parameters d/δ and L/(2a) required for satisfactory tool measurements are between 0.2 and 5, and ≥2.5, respectively, for typical oil field tubulars. For the pipe's electromagnetic parameters conductivity σ and relative magnetic permeability $$\frac{\mu}{\mu_0}$$

fall in the ranges $$3.9\frac{MS}{m} \leq \sigma \leq 7.4\frac{MS}{m}, \quad \text{Eq. (9)}$$

$$20 \leq \frac{\mu}{\mu_0} \leq 200 \quad \text{Eq. (10)}$$

where $\mu_0$ is the vacuum permeability, while the geometrical parameters of typical casings have ranges $$0.2\ \text{inch} \leq d \leq 0.9\ \text{inch and} \quad \text{Eq. (11)}$$

$$2.4\ \text{inch} \leq ID \leq 9\ \text{inch}. \quad \text{Eq. (12)}$$

A preferred embodiment utilizing the previous parameters suggest the following frequency and transmitter-receiver-spacing ranges:

8.75 Hz ≤ f ≤ 70 Hz and
25 inch ≤ L

The final choice of frequencies, spacings, coil lengths turns, coil turns and winding radii need to be determined based on optimizing the sensitivity of the transimpedance measurement to the desired pipe parameters and based on the requirements of data processing algorithms, all well known to those in this art. In particular there may be multiple receivers at different spacings.

Figure 3:
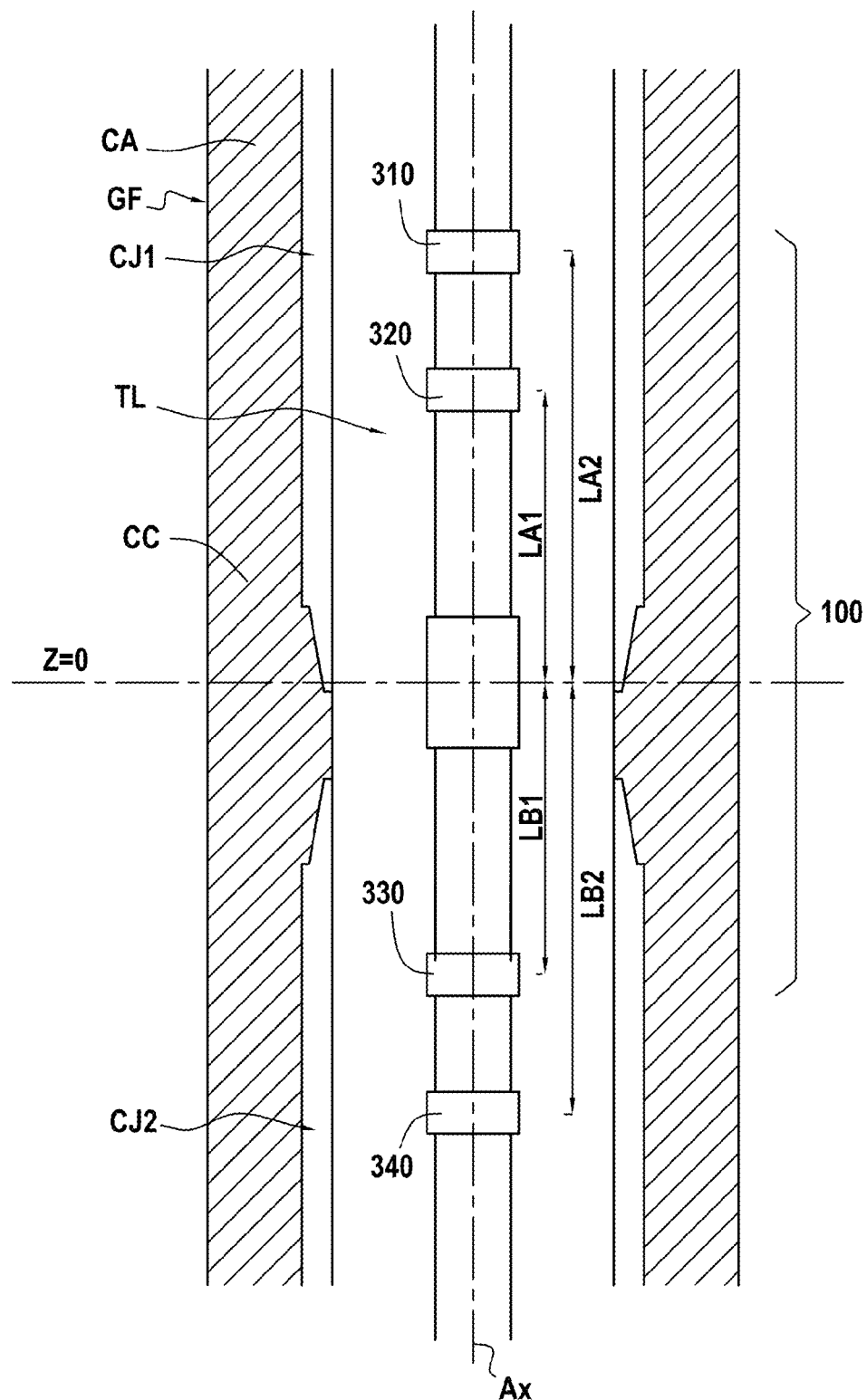
FIG. 3 is a schematic view of a preferred embodiment of the present invention showing two sets of symmetrically spaced receiver coils on either side of a transmitter coil.

The preferred embodiment of the present invention provides a user selectable frequency f of 8.75, 17.5, 35 and 70 Hz, with a receiver coil spacing on each side of the transmitter coil of L=[−36, −30, +30, +36] inches, with the origin of the z or longitudinal axis shown in FIG. 3 at the transmitter coil.

Note that in this embodiment, receiver coil measurements are done at one frequency selected from a choice of four. Note also, that we have indicated four spacings L associated with the RFEC average EM thickness measurement.

The choice of four receivers, symmetrically spaced above and below the transmitter 300, is illustrated in FIG. 3. They are called Double Coils A (310 at spacing $L_{A1}$=−36" and 320 at spacing $L_{A2}$=−30") and Double Coils B (330 at spacing $L_{B1}$=30" and 340 at spacing $L_{B2}$=36"). The choice for this arrangement allows for the removal of double indication of flaws, the so-called "ghost image" removal, of the RFEC average EM thickness measurements as described below.

The transmitter 300 operates at one of a selection of frequencies such as, 8.75 Hz, 17.5 Hz, 35 Hz, 70 Hz to ensure an operator can optimize the signal-to-noise ratio (SNR) and thickness resolution for a given condition at a well site. While 35 Hz would typically allow the tool to work in a single casing, it may be required to measure at lower frequencies in order to log thick casings or multi-casings.

The following TABLE A summarizes coil specifications and typical signal levels of transmitter currents and receiver voltages for this embodiment of the apparatus described herein.

TABLE A

| Transmitter Coil | Number of coils | Length [inch] | Mean radius [inch] | Turns | DC resistance [Ohm] | rms Signal Level [A] |
|---|---|---|---|---|---|---|
| 300 | 1 | 14 | 0.76 | 7550 | 61 | 0.5 @ 35 Hz |

| Receiver Coils | Number of coils | Length [inch] | Mean radius [inch] | Turns | DC resistance [Ohm] | rms Signal Level [V] |
|---|---|---|---|---|---|---|
| 310, 320, 330, 340 | 4 | 3 | 0.56 | 9275 | 7035 | 1e−3 @ 35 Hz |

Mean coil radius is the average value of inner and outer coil diameter. All values at 20° C.

Having defined the operational ranges and design parameters of all sensors, we discuss the processing concepts below.

Removal of Double Indication of Flaws

Figure 4:
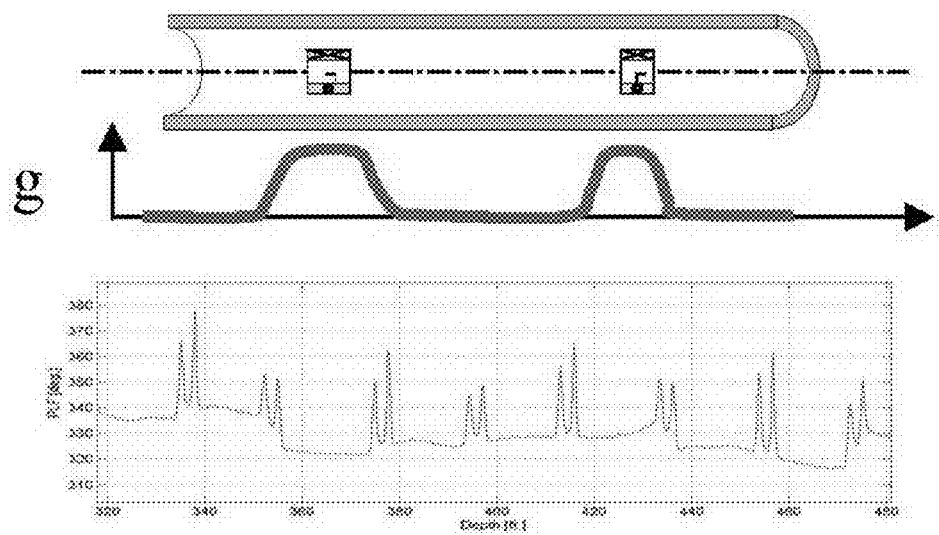
FIG. 4 describes a composite schematic graph of response function (G) of a TX-RX coil pair in a casing superimposed over a graph showing "ghost images" in the transimpedance phase PLF observed on existing tools attenuating phase responses in the presence of casing collars with each collar identified with a ghost image due to the two-peaked response function.

As the apparatus moves through step-like changes of EM-thickness such as passing through casing collars, instead of observing one phase deviation of a given transimpedance due to the local increase of metal, the variation is present two times, once the transmitter is approaching the collar, and a second time when the receiver is viewing the same collar (see FIG. 4). This is due to the geometrical factor that is concentrated within the casing radially and located around the transmitter and receiver in the z-direction. This undesired ghost-image artifact hinders the interpretation of EM thickness measurements in such tools.

The phase shift (σ) of the transimpedance responds to variations of EM thickness like a convolution up to first order:

$$\sigma(z) = \int dy \cdot (h_T(y-z_T) + h_R(y-z_R)) \cdot th(y) \quad \text{Eq. (13)}$$

where th(y) is the thickness (function of depth y), $h_R$ and $h_T$ are the responses of the receiver coil and transmitter coil with positions $z_R$ and $z_T$, respectively. This approximation assumes there are neither major contributions from the casing electromagnetic properties, nor strong variations of the casing inner diameter in the region of interest.

Different designs for the transmitter coils and receiver coils are useful. Therefore, the functions $h_R$ and $h_T$ will be different. Accordingly, receivers located on each side of the transmitter are preferably equivalent receivers, symmetrically placed. As shown in FIG. 3, therefore, coil 310 will be equivalent to coil 340, and coil 320 will be equivalent to coil 330. In the present embodiment, each of these coils is identical. With such a tool configuration, at each tool position, the phase shift measured between transmitter and the first receiver could be compared with phase shift measured between transmitter and second receiver when the tool is translated to the position where transmitter lies on previous position of the first receiver and the second receiver lies at the previous position of the transmitter. In particular, the average of these two phase-shifts will follow the following equation:

$$\frac{1}{2}(\varphi_1(z) + \varphi_2(z)) =$$

$$\frac{1}{2}\int dy \cdot \{(h_T(y-z_T) + h_{R1}(y-z_T)) + (h_T(y-z_R) + h_{R2}(y-z_R))\} \cdot th(y)$$

So if a receiver's impulse responses could be approximated as being equal, the impulse response can be approximated as:

$$g = \tilde{h}(y - z_T) + \tilde{h}(y - z_R) = \tilde{h} \otimes \frac{\delta(y - z_T) + \delta(y - z_R)}{2} \quad \text{Eq. (14)}$$

This combined impulse response $\tilde{h}$ contains contributions of $h_R$ and $h_T$. Furthermore, last equation is formally equivalent of saying that measured phase shift is the convolution of two Dirac deltas with metal thickness convoluted with $\tilde{h}$. And we can conclude that taking the average of phase shifts with appropriate tool translation is a way to handle unsymmetry between transmitter and receivers impulse functions. In this specification, each coils impulse response will be considered equal.

The ghost image removal algorithm is designed to use several receiver-transmitter (RX-TX) spacings to deconvolve σ using data at different spacings and at different "measurement times" i.e. tool positions. The objective is to remove the two delta functions in equation (14) and to replace them with a single function. This allows the apparatus to determine the exact position of each imperfection in the casing.

Consider first a solution proposed for two spacings, L1 and L2. Suppose that:

$$L1 = k1 \times dz \quad \text{Eq. (15)}$$

$$L2 = k2 \times dz \quad \text{Eq. (16)}$$

where dz is a multiple of the vertical sampling and (k1, k2) are integers with no common divisors. Let us sample the response function at the same sampling interval dz. For the spacing L1, we have for instance:

$$\varphi(z_i) = \alpha_T(z_i) + \alpha_R(z_i + L1) = \alpha_T(i) + \alpha_R(i + k1) \quad \text{Eq. (17)}$$

The problem expresses itself as a linear system linking observations ($\varphi$) with the convolution of thickness with impulse responses of the transmitter and receiver ($\alpha_T$ and $\alpha_R$).

Figure 5:
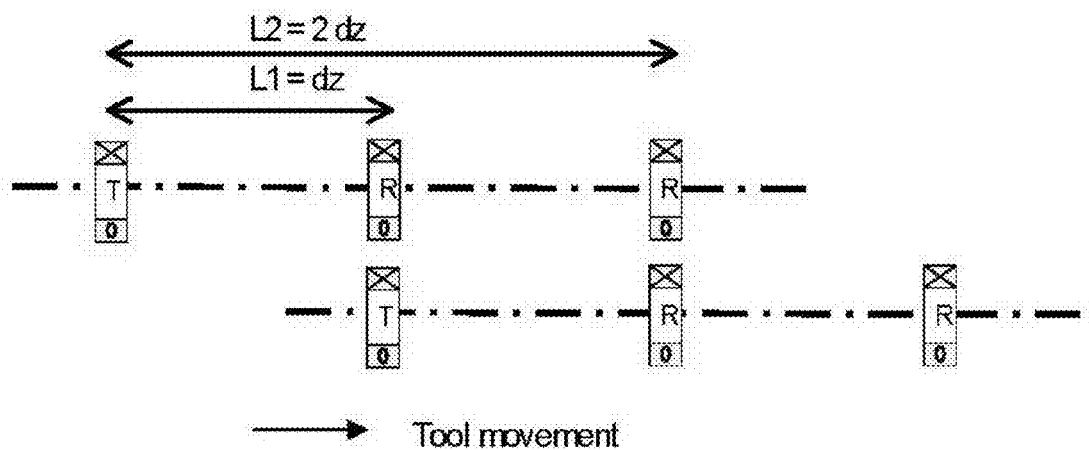
FIG. 5 shows a composite schematic example of a spaced tool arrangement, the top panel showing the transmitter and the two receiver coils at one position, and after the tool is moved to the right by an increment dz, the coils are shifted to the positions shown in the bottom panel.
Figure 6:
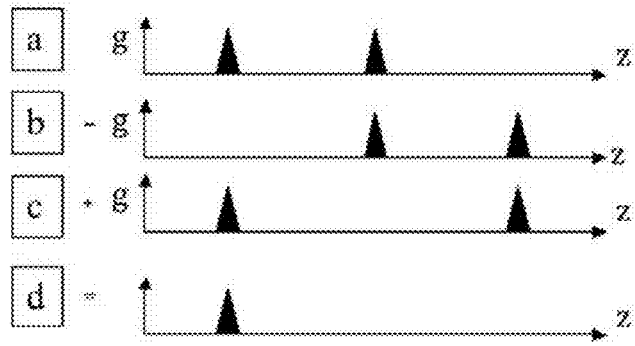
FIG. 6 is a schematic graphical representation of a combination of impulse responses for the tool example shown in FIG. 5 in order to eliminate the double-peaked response of a single transmitter-receiver (TX-RX) pair.

As an example, we may consider the case k1=1 and k2=2. The corresponding tool arrangement is shown schematically in FIG. 5. FIG. 6 is a schematic representation of a combination of impulse responses for the tool example with k1=1 and k2=2 as shown in FIG. 5 in order to eliminate the double-peaked response of a single TX-RX pair. The top (a) shows the response associated with the transmitter and a receiver coil at spacing L1=dz at one log position. After the tool moved to the right by an increment dz the response of the same TX-RX pair in the shifted position is shown in the middle (b). The third line of the graph shows the response associated with the transmitter and a receiver coil at spacing L2=2dz at the initial log position. Finally, the bottom graph (d) is the linear combination of the responses (a)−(b)+(c), which exhibits only a single peak, i.e. no ghost-image response.

One of the solutions to the problem of removing the double indication of flaws is shown in FIG. 6. In this case a linear combination of two responses of the short-spacing coil pair (L1=dz) at different sampling positions 0 and +dz and of the response of the long-spacing coil pair (L2=2dz) provides the desired result. The three ways of forming a single-peak response can be represented by $$f_1 = g(0,L1) - g(dz,L1) + g(0,L2)$$

$$f_2 = g(0,L1) + g(dz,L1) - g(0,L2)$$

$$f_3 = -g(0,L1) + g(dz,L1) + g(0,L2) \quad \text{Eq. (17)}$$

A simple way to obtain the solutions is to create the matrix S $$S = \begin{pmatrix} .5 & .5 & 0 \\ 0 & .5 & .5 \\ .5 & 0 & .5 \end{pmatrix} \quad \text{Eq. (18)}$$

corresponding to the response function linked to the delta functions of eq. 14 where each column represents a position in units of the sampling interval dz. The first two rows correspond to the short-spacing coil pair (L1=dz) at different sampling positions 0 and +dz and the third row corresponds to the response of the long-spacing coil pair (L2=2dz) at position 0.

Inspecting the inverse of the matrix S $$(S)^{-1} = \begin{pmatrix} 1 & -1 & 1 \\ 1 & 1 & -1 \\ -1 & 1 & 1 \end{pmatrix} \quad \text{Eq. (19)}$$

one can identify the coefficients of the solutions given by equations eqs. (17). In general, if several measurements with the fixed coil spacings and with some depth shifting (multiples of dz) are considered, a system of equations can be created and solved using techniques well known in this art.

To adapt the ghost-removal processing to the requirements of RFEC tools regarding minimal spacing L/(2a) 2.5, maximal spacing limited by SNR, sampling interval or other constraints it is possible to find other tool arrangements characterized by (k1, k2).

Another particular embodiment of the invention which satisfies all the above conditions may be k1=5 and k2=6, where dz=6 inches. In this case matrix S and its inverse take the form $$S = \begin{pmatrix} .5 & 0 & 0 & 0 & 0 & .5 & 0 & 0 & 0 & 0 & 0 \\ 0 & .5 & 0 & 0 & 0 & 0 & .5 & 0 & 0 & 0 & 0 \\ 0 & 0 & .5 & 0 & 0 & 0 & 0 & .5 & 0 & 0 & 0 \\ 0 & 0 & 0 & .5 & 0 & 0 & 0 & 0 & .5 & 0 & 0 \\ 0 & 0 & 0 & 0 & .5 & 0 & 0 & 0 & 0 & .5 & 0 \\ 0 & 0 & 0 & 0 & 0 & .5 & 0 & 0 & 0 & 0 & .5 \\ .5 & 0 & 0 & 0 & 0 & 0 & .5 & 0 & 0 & 0 & 0 \\ 0 & .5 & 0 & 0 & 0 & 0 & 0 & .5 & 0 & 0 & 0 \\ 0 & 0 & .5 & 0 & 0 & 0 & 0 & 0 & .5 & 0 & 0 \\ 0 & 0 & 0 & .5 & 0 & 0 & 0 & 0 & 0 & .5 & 0 \\ 0 & 0 & 0 & 0 & .5 & 0 & 0 & 0 & 0 & 0 & .5 \end{pmatrix} \quad (20)$$

$$(S)^{-1} = \begin{pmatrix} 1 & -1 & -1 & -1 & -1 & -1 & 1 & 1 & 1 & 1 & 1 \\ 1 & 1 & -1 & -1 & -1 & -1 & -1 & 1 & 1 & 1 & 1 \\ 1 & 1 & 1 & -1 & -1 & -1 & -1 & -1 & 1 & 1 & 1 \\ 1 & 1 & 1 & 1 & -1 & -1 & -1 & -1 & -1 & 1 & 1 \\ 1 & 1 & 1 & 1 & 1 & -1 & -1 & -1 & -1 & -1 & 1 \\ 1 & 1 & 1 & 1 & 1 & 1 & -1 & -1 & -1 & -1 & -1 \\ -1 & 1 & 1 & 1 & 1 & 1 & 1 & -1 & -1 & -1 & -1 \\ -1 & -1 & 1 & 1 & 1 & 1 & 1 & 1 & -1 & -1 & -1 \\ -1 & -1 & -1 & 1 & 1 & 1 & 1 & 1 & 1 & -1 & -1 \\ -1 & -1 & -1 & -1 & 1 & 1 & 1 & 1 & 1 & 1 & -1 \\ -1 & -1 & -1 & -1 & -1 & 1 & 1 & 1 & 1 & 1 & 1 \end{pmatrix} \quad (21)$$

We find again that several solutions are possible, and among them, only one has the property of having the same weight applied on all short spacings and all long spacings. The combination is simply the sum of all short spacing measurements minus all long spacing measurements that are around one depth with an interval of length (k1+k2)*dz. In the above example, this specific solution is the 6-th row of coefficients $$(S)_6^{-1} = (1\ 1\ 1\ 1\ 1\ 1\ -1\ -1\ -1\ -1\ -1) \quad (22)$$

This processing scheme is an averaging of short spacing minus average of long spacing, which explains why this scheme is robust to Gaussian noise.

As explained previously, the tool is symmetrized by addition of symmetrically placed receivers, and de-ghosting algorithm is applied on symmetrized phase shifts (taking the average phase shift when flipping TX and RX positions).

Figure 7:
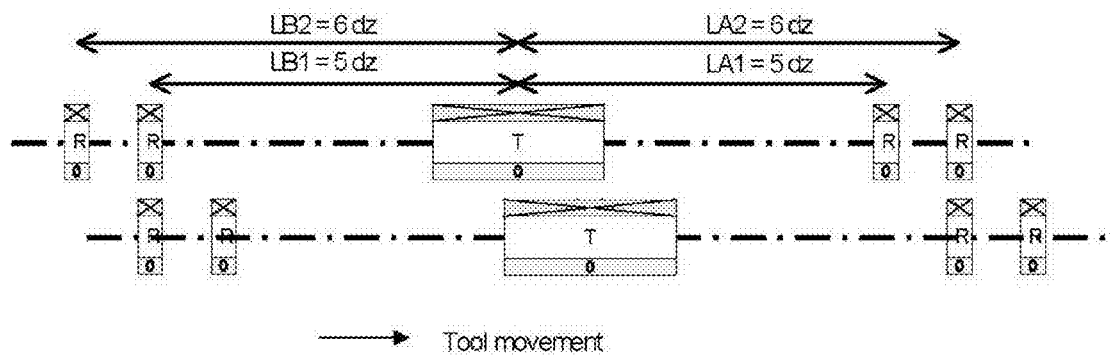
FIG. 7 is a schematic example of a symmetric tool arrangement with k1=5 and k2=6 on both sides of the central transmitter.
Figure 8:
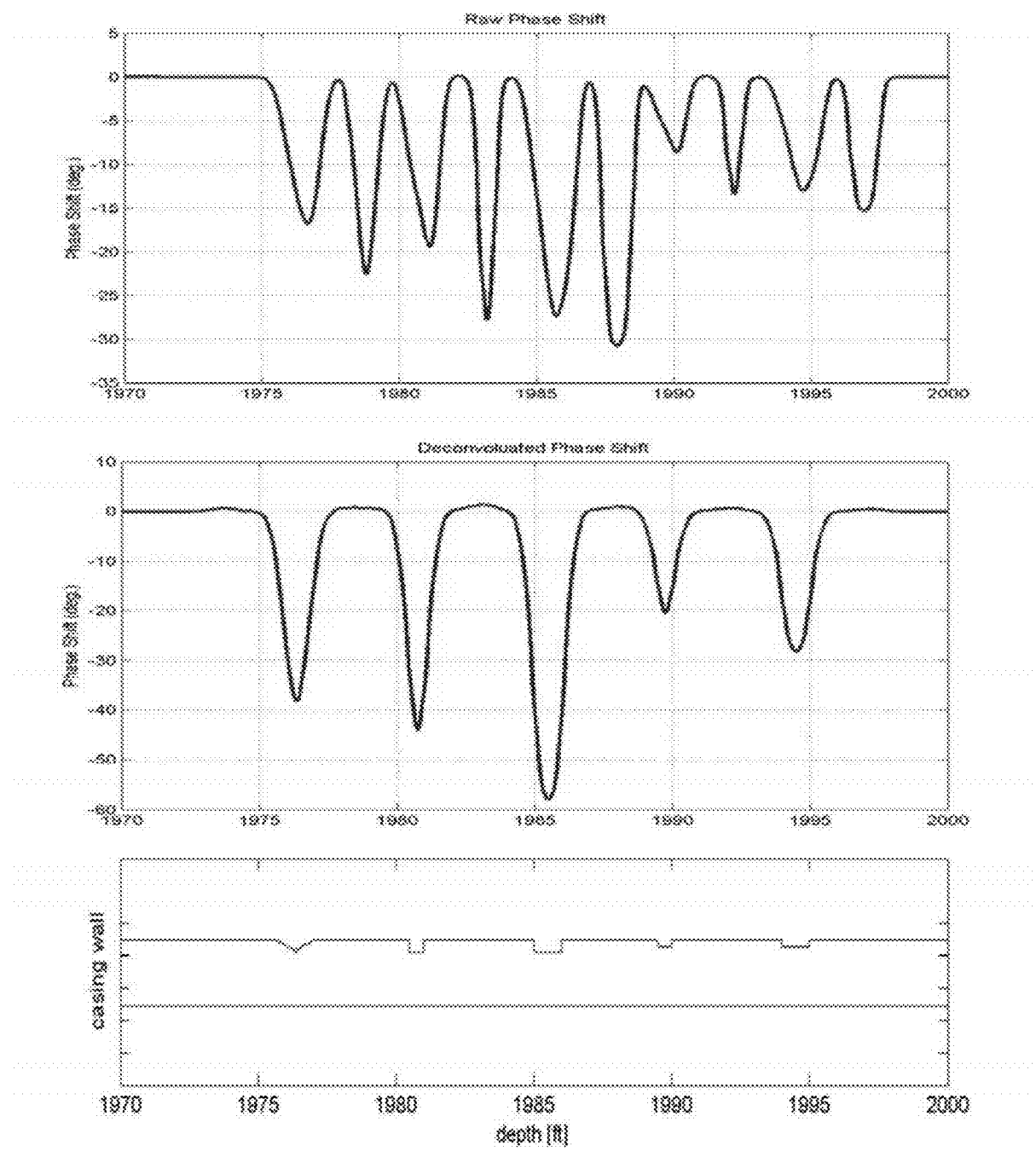
FIG. 8 is an example of ghosting-image removal processing showing the "raw" response (in the top panel) calculated with five groove defects in the casing wall (shown at bottom panel).

A preferred embodiment of this symmetrical tool arrangement, using only two pairs of symmetric TX-RX spacings, is shown in FIG. 7. In this case k1=5 and k2=6, where dz=6 inches. It corresponds to the design parameters given above. An example of the processing results using the solution of eq. (22) is shown in FIG. 8. One can generalize the algorithm to larger number of spacing arrangements. Using spacings with a ratio of large integers increases in the noise amplification in the processing.

Numerous embodiments and alternatives thereof have been disclosed. While the above disclosure includes the best mode belief in carrying out the invention as contemplated by the named inventors, not all possible alternatives have been disclosed. For that reason, the scope and limitation of the present invention is not to be restricted to the above disclosure, but is instead to be defined and construed by the appended claims.

What is claimed is:

1. An apparatus for measuring ferromagnetic tubular thickness using remote field eddy current sensing comprising:
    a tool body suitable for insertion in a tubular, wherein the tool body comprises a transmitter coil and a plurality of receiver devices, wherein each receiver device of the plurality of receiver devices is situated on opposing sides of the transmitter coil, and wherein each receiver device is coil centered on a longitudinal axis of the apparatus;
    a circuit for energizing the transmitter coil at a selectable frequency; and
    a circuit for receiving a signal from each receiver device.

2. The apparatus of claim 1 wherein the circuit is suitable for processing the signal from each receiver device to eliminate a double indication of flaws.

3. The apparatus of claim 1 wherein the circuit is a programmable digital computer providing a central processor, a memory and connections to an analog to digital convertor for digitizing the signal to discrete data for processing by the programmable digital computer.

4. The apparatus of claim 1 wherein the circuit is suitable for correlating a current of the transmitter with the signal received from each receiver device, as the apparatus is moved through the tubular.

5. The apparatus of claim 4 wherein the circuit is suitable for measuring phase deviations of a transimpedance as the apparatus moves past a substantially same point in the tubular such that a duplicate image is eliminated.

6. The apparatus of claim 5 wherein the circuit is suitable for averaging impulses transmitted and received by the transmitter coil to lower a signal to noise ratio for the signal measured from each receiver device.

7. The apparatus of claim 1 wherein the frequency is selectable between 8.75, 17.5, 35, and 70 Hz.

8. The apparatus of claim 1 wherein the receiver coils are spaced a distance which, when divided by the inner diameter of the tubular, is greater than or equal to 2.5.

9. The apparatus of claim 1 wherein the plurality of symmetrically spaced receiver coils is comprised of four coils, each pair spaced on each side of the transmitter coil a distance of L1=k1×dz and L2=k2×dz, where k1 and k2 have no common divisor and dz is an incremental length along the longitudinal axis of the apparatus.

10. The apparatus of claim 1 wherein the receiver devices are selected from the one of the following: coils, Hall effect voltage detectors, and magnetoresistive sensors.

11. An apparatus for measuring defects in a well bore pipe using remote field eddy current measurement comprising:
    a transmitter coil and a plurality of receiver coils in spaced axial relationship from each other, wherein each of the plurality of receiver coils are spaced a distance apart which, when divided by an inner diameter of the well bore pipe, is greater than or equal to 2.5;
    a circuit suitable for:
        generating a transmitter current;
        sensing a receiver voltage at each receiver coil of the plurality of receiver coils; and
        collecting a convoluted signal proportional to a thickness of the pipe adjacent each receiver coil; and
    a data analysis circuit which deconvolves the convoled signal to remove ghost-image signals.

12. The apparatus of claim 7 wherein the receiver coils are symmetrically located on opposing sides of the transmitting coil.

13. A method of removing ghost defects from a remote field eddy current sensing device comprising:
    generating from a transmitter an eddy current on a tubular outer surface at a first position;
    detecting the eddy current signal from the first position with more than one remote receiver;
    generating an eddy current signal on a tubular outer surface at a second position;
    detecting the eddy current from the second position with the more than one remote receiver;
    determining a linear combination of eddy current signals detected by the more than one remote receiver to eliminate ghost defects in the eddy current signals.

14. The method of claim 13, comprising exciting the transmitting with a low frequency current to generate the eddy current in the tubular outer surface.

15. The method of claim 13, comprising storing the detected eddy current signal from the first position.

16. The method of claim 15, comprising storing the detected eddy current signal from the second position.

17. The method of claim 13, comprising:
    repeatedly moving the transmitter in the tubular to a different position;
    generating an eddy current signal on a tubular outer surface at a different position; and
    detecting the eddy current from the different position with the more than one remote receiver.

18. The method of claim 13 wherein the more than one remote receiver comprises four equal coils placed on opposing sides of a transmitter and spaced a distance L from the transmitter, wherein L is at least 2.5 times an inner diameter of the tubular and wherein an electromagnetic thickness of the tubular is less than or equal to 5.

* * * * *